(12) United States Patent
Favero et al.

(10) Patent No.: US 12,269,789 B2
(45) Date of Patent: Apr. 8, 2025

(54) METHOD FOR OBTAINING BIO-SOURCED N-VINYLFORMAMIDE (71) Applicant: SNF Group, Andrezieux Boutheon (FR)

(72) Inventors: Cédrick Favero, Andrezieux Boutheon (FR); Johann Kieffer, Andrezieux Boutheon (FR)

(73) Assignee: SNF Group, Andrezieux Boutheon (FR)

( * ) Notice: Subject to any disclaimer, the term of this patent is extended or adjusted under 35 U.S.C. 154(b) by 0 days.

(21) Appl. No.: 18/566,281

(22) PCT Filed: Jul. 8, 2022

(86) PCT No.: PCT/EP2022/069153
§ 371 (c)(1),
(2) Date: Dec. 1, 2023

(87) PCT Pub. No.: WO2023/281086
PCT Pub. Date: Jan. 12, 2023

(65) Prior Publication Data
US 2024/0270681 A1 Aug. 15, 2024

(30) Foreign Application Priority Data
Jul. 9, 2021 (FR) ..................................... 2107497

(51) Int. Cl.
*C07C 233/03* (2006.01)
*C07C 231/12* (2006.01)
(Continued)

(52) U.S. Cl.
CPC .......... *C07C 233/03* (2013.01); *C07C 231/12* (2013.01); *C08F 226/02* (2013.01);
(Continued)

(58) Field of Classification Search
None
See application file for complete search history.

(56) References Cited

U.S. PATENT DOCUMENTS 3,056,833 A 10/1962 Heath
3,822,306 A 7/1974 Becke et al.
(Continued)

FOREIGN PATENT DOCUMENTS

FR 2979821 A1 3/2013
WO WO 2016/020622 A1 2/2016
WO WO 2018/108608 A1 6/2018

OTHER PUBLICATIONS

Allison et al., "Reference and Intercomparison Materials for Stable Isotopes of Light Elements", International Atomic Energy Agency, 1995, in 159 pages.
(Continued)

*Primary Examiner* — Sudhakar Katakam
*Assistant Examiner* — Jennifer C Sawyer
(74) *Attorney, Agent, or Firm* — Knobbe, Martens, Olson & Bear, LLP (57) ABSTRACT A method for obtaining N-vinylformamide including the reaction between an acetaldehyde and a formamide, one of the two, preferably both, being at least partially renewable and non-fossil. A bio-sourced N-vinylformamide monomer, a bio-sourced polymer obtained by polymerization including at least N-vinylformamide monomer, and the use of the polymer in various technical fields.

3 Claims, 1 Drawing Sheet (51) Int. Cl.
 *C08F 226/02* (2006.01)
 *D21H 17/34* (2006.01)
 *D21H 23/04* (2006.01)

(52) U.S. Cl.
 CPC ............ *D21H 17/34* (2013.01); *D21H 23/04* (2013.01); *C08F 2800/20* (2013.01)

(56) References Cited

U.S. PATENT DOCUMENTS

| | | |
|---|---|---|
| 4,567,300 A | 1/1986 | Murao et al. |
| 4,818,505 A | 4/1989 | Muller |
| 4,906,777 A | 3/1990 | Pinschmidt, Jr. et al. |
| 5,527,963 A * | 6/1996 | Sato ..................... C07C 231/12 564/187 |
| 2018/0057445 A1 | 3/2018 | Dumoleijn et al. |

OTHER PUBLICATIONS

Decision to grant patent issued in in EP Patent Application No. 22747016.8, dated Oct. 26, 2023.
International Search Report and Written Opinion issued in International Application No. PCT/EP2022/069153, mailed on Oct. 26, 2022.
Roessler et al., "Time-Resolved Liquid Scintillation Counting", Liquid Scintillation Counting and Organic Scintillators, 1991, pp. 501-511.

\* cited by examiner

METHOD FOR OBTAINING BIO-SOURCED N-VINYLFORMAMIDE

FIELD OF THE INVENTION

The present invention relates to a method for obtaining bio-sourced N-vinylformamide comprising the reaction between an acetaldehyde and a formamide, one of the two, preferably both, being at least partially renewable and non-fossil. The invention relates to the bio-sourced N-vinylformamide monomer as well as a bio-sourced polymer obtained from at least one bio-sourced N-vinylformamide monomer according to the invention. Lastly, the invention relates to the use of the invention's bio-sourced polymers in various technical fields.

PRIOR ART

Ethylenically unsaturated monomers, such as N-vinylformamide are widely used in manufacturing water-soluble polymers.

N-vinyformamide (NVF) is obtained according to the reaction diagram hereinafter.

Several variants exist depending on the HX protecting agent used. NVF is generally synthesized by the so-called "alkoxy" process in which the protective agent is an alcohol and more preferably methanol. The synthesis takes place in two steps, starting with hydroxyethylformamide obtained from acetaldehyde and formamide. The hydroxyethylformamide is then converted into methoxyethylformamide by reaction with methanol and a catalyst. The methoxyethylformamide is then pyrolyzed at high temperature to obtain N-vinylformamide.

Acetaldehyde is a raw material obtained from oxidation of ethylene as described in the Wacker method. Ethylene is a fossil-based olefin, and is currently produced by steam cracking of naphtha, itself derived from crude oil refining. More recently, and with the advent of shale gas production, various ethane dehydrogenation methods have been described to produce ethylene.

Fossil-based ethylene contains various impurities, which remain or are transformed by the Wacker method. Additionally, acetaldehyde tends to oxidize to acetic acid due to the presence of oxygen in the Wacker method.

Formamide is obtained from the reaction of formic acid with ammonia. Formic acid is fossil-based and obtained from the reaction between ethane and oxygen, as described in document U.S. Pat. No. 3,056,833.

Document U.S. Pat. No. 4,567,300 describes the formation of hydroxyethyl formamide in the presence of acetaldehyde and formamide. In order to counteract the presence of acidity in fossil-based acetaldehyde, the addition of a base, in this case potassium carbonate, is described in order to allow a good conversion of the reactants and to obtain good quality hydroxyethylformamide.

Other variants for obtaining N-vinylformamide have been described, such as the so-called "hydrocyanic acid" process, particularly in document U.S. Pat. No. 3,822,306. In this case, the protective agent is hydrocyanic acid which is reacted with acetaldehyde. The yield is limited to 75% and involves hydrocyanic acid, which is a very toxic compound. It is also possible to obtain N-vinyl formamide according to another variant known as "bis ethylene formamide", described document in U.S. Pat. No. 4,906,777 for example.

In all cases, the three carbons of N-vinylformamide are derived from acetaldehyde and formamide.

In order to counteract the use of raw materials with a high proportion of impurities leading to lower quality N-vinylformamide, strategies for purifying N-vinylformamide have been described.

Document U.S. Pat. No. 4,818,505 describes a fractional distillation method on a column, operated under very high vacuum (0.5 mbar or 1 bar=$10^5$ Pa) in order to separate the unreacted formamide from the previous steps and the N-vinylformamide. The mixture to be separated must be heated to high temperature. N-vinylformamide being by nature a reactive monomer, a fraction of the mixture to be separated polymerizes, which results in a loss of yield, in the generation of a polymer which must be destroyed and in a loss of productivity of the production unit (induced by the stoppage of the distillation column for cleaning purposes).

Document WO 2018/108608 A1 discloses a polymer comprising: (a) from 9.49 to 98 mol-% units of Formula [$CH_2$—$CR^1$((C=O)—$NR^2$-A-$SO_2$—$O^-Q^+$)] wherein at least 10 wt.-% of these units of Formula (1) comprise from 28 wt.-% to 100 wt.-% bio-sourced carbon content; (b) from 0.01 mol-% to 5 mol-% crosslinking or branching units; (c) from 0.01 mol-% to 88.52 mol-% of repeating neutral structural units; (d) from 1.98 mol-% to 20 mol-% of repeating anionic structural units. Document WO 2018/108608 A1 does not teach a polymer comprising bio-sourced N-vinylformamide.

Document US 2018/057445 relates to processes for the production of N-vinylcarboxylic acid amides, for instance N-vinylformamide and its intermediates. It does not describe the use of bio-sourced compounds.

The problem the invention proposes to resolve is to propose a new and improved polymer obtained from a bio-sourced N-vinylformamide monomer.

SUMMARY OF THE INVENTION

Surprisingly, the applicant has observed that the use of acetaldehyde and formamide, one of the two, preferably both, being at least partially renewable and non-fossil, and preferably totally renewable, in a method for obtaining N-vinylformamide, allows to substantially improve the quality of the monomer obtained, thereby improving its polymerization and the application performance of the polymers obtained.

The applicant has particularly observed this improvement where the method is a method for obtaining N-vinylformamide by the "alkoxy" process, particularly where the alcohol used as a protective agent is methanol or isopropanol, preferably methanol.

Without seeking to be bound by any particular theory, the Applicant raises the possibility that the different nature of the impurities between fossil-based acetaldehyde and renewable and non-fossil-based acetaldehyde, and/or between fossil-based formamide and renewable and non-fossil formamide is the cause of these unexpected technical effects.

"A and/or B" is understood to mean according to invention A, or B, or A and B.

First and foremost, the invention relates to a method for obtaining N-vinylformamide comprising the reaction between an acetaldehyde and a formamide, one of the two, preferably both, being at least partially renewable and non-fossil.

The invention further relates to the N-vinylformamide with a bio-sourced carbon content ranging between 5 wt % and 100 wt % relative to the total carbon mass in said N-vinylformamide, the bio-sourced carbon content being measured according to ASTM D6866-21 Method B.

The invention also relates to a polymer obtained by polymerization of at least one N-vinylformamide monomer obtained according to the method of the invention or as described, and the use of said polymer in various technical fields.

With the present invention, it is possible to achieve environmental objectives inherent in new technical innovations. In the present case, the use of renewable raw material, in this case acetaldehyde and/or formamide, helps to significantly optimize the conversion process and the quality of the monomer obtained.

As compared to fossil formamide, the Applicant has observed that the bio-sourced nature of formamide allows better conversion to N-vinylformamide, and generates fewer impurities.

As compared to fossil compounds, the Applicant has also observed that the percentage of conversion of formamide is greater when acetaldehyde is at least partly of renewable and non-fossil origin.

As compared to fossil compounds, the Applicant has also observed that the use of formamide partially or totally of renewable and non-fossil origin, and of acetaldehyde partially or totally of renewable and non-fossil origin improves the method for obtaining N-vinylformamide.

The Applicant has also observed that polymers according to the invention, obtained from partially or totally bio-sourced monomers are more easily biodegradable than polymers obtained from fossil monomers.

The Applicant has also observed that, in addition to better drainage performance, polymers according to the invention exhibit dry strength performance at least equivalent or even better than that of polymers obtained from fossil monomers.

DETAILED DESCRIPTION OF THE INVENTION

In the context of the invention, the terms "renewable and non-fossil" are used to designate the origin of a chemical compound derived from biomass or from synthesis gas (syngas), i.e. resulting from one or more chemical transformations carried out on one or more natural and non-fossil raw materials. The terms "bio-sourced" or "bio-resourced" can also be used to characterize the renewable and non-fossil origin of a chemical compound. The renewable and non-fossil origin of a compound includes renewable and non-fossil raw materials stemming from the circular economy, which have been previously recycled, once or several times, in a biomass material recycling process, such as materials from polymer depolymerization or pyrolysis oil processing.

According to the invention, the "at least partially renewable and non-fossil" quality of a compound means a bio-sourced carbon content preferably between 5 wt % and 100 wt % relative to the total carbon weight of said compound.

In the context of the invention, the ASTM D6866-21 standard Method B is used to characterize the bio-sourced nature of a chemical compound and to determine the bio-sourced carbon content of said compound. The value is expressed as a weight percentage (wt %) of bio-sourced carbon relative to the total carbon weight in said compound.

The ASTM D6866-21 standard is a test method that teaches how to experimentally measure the bio-sourced carbon content of solids, liquids and gaseous samples by radiocarbon analysis.

This standard primarily uses Accelerator Mass Spectrometry (AMS) technology. This technique is used to naturally measure the radionuclides present in a sample, wherein the atoms are ionized, then accelerated to high energies, then separated, and individually counted in Faraday cups. This high-energy separation is extremely effective at filtering out isobaric interference, so that AMS is able to accurately measure abundances of carbon-14 relative to carbon-12 (14C/12C) to an accuracy of 1.10-15.

The ASTM D6866-21 standard Method B uses AMS and IRMS (Isotope Ratio Mass Spectroscopy). The test method allows to directly differentiate contemporary carbon-based carbon atoms from fossil-based carbon atoms. A measure of the carbon-14 to carbon-12 or carbon-14 to carbon-13 content of a product is determined against a modern carbon-based reference material accepted by the radiocarbon dating community such as the NIST's Standard Reference Material (SRM) 4990C (oxalic acid).

The sample preparation method is described in the standard and does not require any special comment as it is a commonly used procedure.

Analysis, interpretation and reporting of results are described below. Isotope ratios of carbon-14 to carbon-12 content or carbon-14 to carbon-13 content are measured using AMS. Isotope ratios of carbon-14 to carbon-12 content or carbon-14 to carbon-13 content are determined relative to a standard traceable via the NIST SRM 4990C modern reference standard. The "fraction of modern" (fM) represents the amount of carbon-14 in the tested product relative to the modern standard. It is most often referred to as percent modern carbon (pMC), the percentage equivalent to fM (e.g. fM 1=100 pMC).

All pMC values obtained from radiocarbon analyses must be corrected for isotopic fractionation using a given stable isotope. The correction should be made using the carbon-14 to carbon-13 values determined directly using the AMS where possible. If this is not possible, the correction should be made using the delta 13C ($\delta 13C$) measured by IRMS, CRDS (Cavity Ring Down Spectroscopy) or any other equivalent technology that can provide accuracy to within plus or minus 0.3 per thousand.

"Zero pMC" represents the total absence of measurable 14C in a material above the background signals, thus indicating a fossil (e.g. petroleum-based) carbon source. A value of 100 pMC indicates a fully "modern" carbon source. A pMC value between 0 and 100 indicates a proportion of carbon derived from a fossil source relative to a "modern" source.

The pMC may be higher than 100% due to the persistent, but diminishing, effects of 14C injection into the atmosphere caused by atmospheric nuclear testing programmes. The pMC values need to be adjusted by an atmospheric correction factor (REF) to obtain the actual bio-sourced content of the sample.

The correction factor is based on the excess 14C activity in the atmosphere at the time of testing. A REF value of 102 pMC was determined for 2015 based on $CO_2$ measurements in the air in a rural area of the Netherlands (Lutjewad, Groningen). The first version of this standard (ASTM D6866-04) in 2004 had referenced a value of 107.5 pMC, while the later version ASTM D6866-10 (2010) had referenced a value of 105 pMC. These data points represent a drop of 0.5 pMC per year. Consequently, on 2 January of each year, the values in Table 1 below were used as REF value until 2019, reflecting the same decrease of 0.5 pMC per year. The REF values (pMC) for 2020 and 2021 have been determined to be 100.0 based on continuous measurements in the Netherlands (Lutjewad, Groningen) until 2019. References for reporting carbon isotope ratio data are provided below for 14C and 13C, respectively Roessler, N., Valenta, R. J., and van Cauter, S., "Time-resolved Liquid Scintillation Counting", *Liquid Scintillation Counting and Organic Scintillators*, Ross, H., Noakes, J. E., and Spaulding, J. D., Eds., Lewis Publishers, Chelsea, M I, 1991, pp. 501-511. Allison, C. E., Francy, R. J., and Meijer, H. A. J., "Reference and Intercomparison Materials for Stable Isotopes of Light Elements", International Atomic Energy Agency, Vienna, Austria, *IAEATECHDOC*-825, 1995.

The percentage of the bio-sourced carbon content is calculated by dividing pMC by REF and multiplying the result by 100. For example, [102 (pMC)/102 (REF)]× 100=100% bio-sourced carbon. The results are indicated as a weight percentage (wt %) of bio-sourced carbon relative to the total carbon weight in said compound.

TABLE 1

Reference of percentage of modern carbon (pMC)

| REF year | pMC |
|---|---|
| 2015 | 102.0 |
| 2016 | 101.5 |
| 2017 | 101.0 |
| 2018 | 100.5 |
| 2019 | 100.0 |
| 2020 | 100.0 |
| 2021 | 100.0 |

In the context of the invention, the term "segregated" means a material stream that is distinctive and distinguishable from other material streams in a value chain (e.g. in a product manufacturing method), and thus considered to belong to a set of materials having an equivalent nature, such that the same origin of the material, or its manufacture according to the same standard or norm, can be tracked and guaranteed throughout this value chain.

For example, this may be the case of a chemist buying a 100% bio-sourced acetaldehyde exclusively from a single supplier who guarantees the 100% bio-sourced origin of the acetaldehyde delivered, and said chemist processing this 100% bio-sourced acetaldehyde separately from other potential acetaldehyde sources to produce a chemical compound. If the chemical compound produced is made solely from said 100% bio-sourced acetaldehyde, then the chemical compound is 100% bio-sourced.

In the context of the invention, the term "non-segregated", in contrast to the term "segregated", is understood to mean a material stream that cannot be differentiated from other material streams in a value chain.

In order to better understand this notion of segregation, it is useful to recall some basics about the circular economy and its practical application in methods, especially chemical transformation.

According to the French Environment and Energy Management Agency (ADEME), the circular economy can be defined as an economic system of trade and production which, at all stages of the life cycle of products (goods and services), seeks to increase efficiency in the use of resources and to reduce the environmental impact while developing the well-being of individuals. In other words, it is an economic system devoted to efficiency and sustainability that minimizes waste by optimizing value generated by resources. It relies heavily on a variety of conservation and recycling practices in order to break away from the current more linear "take-make-dispose" approach.

In the field of chemistry, which is the science of transforming one substance into another, this translates into reusing material that has already been used to make a product. Theoretically, all chemicals can be isolated and therefore recycled separately from other chemicals. The reality, particularly in industry, is more complex and means that even when isolated, the compound cannot often be differentiated from the same compound originating from another source, thus complicating the traceability of the recycled material.

For this reason, various traceability models have been developed taking into account this industrial reality, thereby allowing users in the chemical industry to manage their material streams with full knowledge of the facts, and allowing end customers to understand and know in a simple way the origin of the materials used to produce an object or a commodity.

These models have been developed to build transparency and trust throughout the value chain. Ultimately, this allows end-users or customers to choose a more sustainable solution without having the ability themselves to control every aspect of the method, by knowing the proportion of a desired component (e.g. of a bio-sourced nature) in an object or commodity.

One such model is "segregation", which we have defined earlier. Some known examples where this model applies are glass and some metals where it is possible to track material streams separately.

However, chemicals are often used in complex combinations, and separate cycles are very often difficult to implement, especially due to prohibitive costs and highly complex stream management, such that the "segregation" model is not always applicable.

Consequently, when it is not possible to differentiate between material streams, other models are applied, which are grouped together under the term "non-segregated" and which entail, for example, taking into account the proportion of a specific stream relative to other streams, without physically separating the streams. One example is the Mass Balance Approach.

The Mass Balance Approach involves accurately tracking the proportion of a category (e.g. "recycled") relative to a whole in a production system in order to guarantee, on the basis of an auditable account ledger, a proportionate and appropriate allocation of the content of that category in a finished product.

For example, this may be the case of a chemist buying a 50% bio-sourced acetaldehyde from a supplier who guarantees, according to the mass or weight balance approach, that in the acetaldehyde delivered, 50% of the acetaldehyde has a bio-sourced origin, and de facto 50% is not of bio-sourced origin, and the use by said chemist of this 50% bio-sourced acetaldehyde with another stream of 0% bio-sourced acetaldehyde, the two streams not being identifiable at some point during the production process, due to mixing for example. If the chemical compound produced is made from 50% bio-sourced 50 wt % guaranteed acetaldehyde, and 0% bio-sourced 50 wt % acetaldehyde, the chemical compound is 25% bio-sourced.

In order to guarantee the stated "bio-sourced" figures, for example, and to encourage the use of recycled raw materials in producing new products, a set of globally shared and standardised rules (ISCC+, ISO 14020) has been developed to reliably manage material streams.

In the context of the invention, the term "recycled" is understood to mean the origin of a chemical compound derived from a method for recycling a material considered as waste, i.e. resulting from one or more transformations carried out using at least one recycling method on at least one material generally considered as waste.

The term "water-soluble polymer" is understood to mean a polymer which gives a clear aqueous solution when dissolved by stirring at 25° C. and with a concentration of 20 $g \cdot L^{-1}$ in water.

Method According to the Invention

The present invention therefore relates to a method for obtaining N-vinylformamide comprising the reaction between an acetaldehyde and a formamide, one of the two, preferably both, being at least partially renewable and non-fossil.

More specifically and preferentially, the compounds used to obtain N-vinylformamide and containing the carbon atoms that will be found in the N-vinylformamide molecule are partially or totally renewable and non-fossil. These compounds are acetaldehyde and formamide.

Acetaldehyde preferably has a bio-sourced carbon content ranging between 5 wt % and 100 wt % relative to the total carbon mass in said acetaldehyde, the bio-sourced carbon content being measured according to ASTM D6866-21 Method B.

Formamide preferably has a bio-sourced carbon content ranging between 5 wt % and 100 wt % relative to the total carbon mass in said formamide, the bio-sourced carbon content being measured according to ASTM D6866-21 Method B.

In the whole invention, the bio-sourced carbon content of a compound for which it is specified that it is at least partially renewable and non-fossil, or for which the bio-sourced carbon content is specified, relative to the total carbon weight in said compound, ranges from 5 wt % to 100 wt %, and preferably from 10 wt % to 100 wt %, preferably from 15 wt % to 100 wt %, preferably from 20 wt % to 100 wt %, preferably from 25 wt % to 100 wt %, preferably from 30 wt % to 100 wt %, preferably from 35 wt % to 100 wt %, preferably from 40 wt % to 100 wt %, preferably from 45 wt % to 100 wt %, preferably from 50 wt % to 100 wt %, preferably from 55 wt % to 100 wt %, preferably from 60 wt % to 100 wt %, preferably from 65 wt % to 100 wt %, preferably from 70 wt % to 100 wt %, preferably from 75 wt % to 100 wt %, preferably from 80 wt % to 100 wt %, preferably from 85 wt % to 100 wt %, preferably from 90 wt % to 100 wt %, preferably from 95 wt % to 100 wt %, preferably from 97 wt % to 100 wt %, preferably from 99 wt % to 100 wt %, the bio-sourced carbon content being measured according to ASTM D6866-21 Method B.

Preferentially, acetaldehyde has a bio-sourced carbon content ranging between 50 wt % and 100 wt %, preferably 100 wt % relative to the total carbon mass in said acetaldehyde, the bio-sourced carbon content being measured according to ASTM D6866-21 Method B.

Preferentially, formamide has a bio-sourced carbon content of 100 wt % relative to the total carbon mass in said formamide, the bio-sourced carbon content being measured according to ASTM D6866-21 Method B.

Preferably, the acetaldehyde is totally renewable and non-fossil. Preferably, the formamide is totally renewable and non-fossil. Preferably, the acetaldehyde and the formamide are totally renewable and non-fossil.

The acetaldehyde and/or the formamide, preferably both, can be non-segregated, partially segregated, or fully segregated.

Where the acetaldehyde and/or the formamide is totally renewable and non-fossil, it may be either:
  a) Totally of recycled origin and
  a)1) Or totally segregated;
  a)2) Or partially segregated;
  a)3) Or non-segregated;
  b) Or partially of recycled origin and
  b)1) Or totally segregated;
  b)2) Or partially segregated;
  b)3) Or non-segregated;
  c) Or totally of non-recycled origin and
  c)1) Or totally segregated;
  c)2) Or partially segregated;
  c)3) Or non segregated.

In these various embodiments, where the acetaldehyde and/or the formamide is partially segregated, the weight ratio between the "segregated" part and the "non-segregated" part is preferably between 99:1 and 10:90, preferably between 99:1 and 30:70, or more preferably between 99:1 and 50:50.

Among these various embodiments, preference is given to the three a) embodiments, the three b) embodiments, and embodiment c)1). Among these embodiments, much greater preference is given to embodiments a)1), a)2), b)1), b)2) and c)1). The two most preferred embodiments are a)1) and b)1).

Preferably, the acetaldehyde and/or the formamide, preferably both, are partially segregated, or totally segregated.

Preferably, the acetaldehyde and/or the formamide, preferably both, are partially segregated, or totally recycled.

The industrial reality is such that it is not always possible to obtain industrial quantities of acetaldehyde and/or formamide that are bio-sourced, totally recycled and/or segregated or highly recycled and segregated. Hence, the above preferences may be more difficult to implement at the moment. From a practical standpoint, embodiments a)3), b)3), and c) are currently implemented more easily and on a larger scale. With techniques evolving quickly towards the circular economy, there is no doubt that the already applicable preferred modes will soon be applicable on a very large scale.

Where the acetaldehyde and/or the formamide is/are partially renewable and non-fossil, a distinction is made between the renewable part (bio-sourced) and the non-bio-sourced part. Obviously, each can be according to the same embodiments a), b) and c) described hereinabove.

As concerns the bio-sourced part of the partially bio-sourced acetaldehyde and/or formamide, the same preferences apply as in the case where the compound is fully bio-sourced.

However, as concerns the non-bio-sourced part of the partially bio-sourced compound, it is even more preferable to have as large a recycled component as possible for a circular economy approach. Hence, in this case, preference is given to embodiments a)1), a)2), b)1), b)2), particularly a)1) and b)1).

Acetaldehyde is preferably obtained either from ethanol derived at least partially, preferably totally, from biomass, or from ethylene derived at least partially, preferably totally, from biomass.

Formamide is preferably obtained either from formic acid derived at least partially, preferably totally, from biomass, or from ethyl formate derived at least partially, preferably totally, from biomass, or from carbon monoxide derived at least partially, preferably totally, from recycling of $CO_2$, which is considered to be a renewable and non-fossil source.

With respect to the reaction between an acetaldehyde and a formamide to form N-vinylformamide, the person skilled in the art may refer to the already established knowledge. Preferentially, the method for obtaining N-vinylformamide is by the "alkoxy" process, particularly when the alcohol used as a protective agent is methanol.

In a first step, acetaldehyde is contacted with formamide in the presence of a solvent and a base. Preferentially, the reaction solvent is toluene, and the base is potassium bicarbonate. The synthesis reactor is filled with a mixture of toluene and acetaldehyde.

The potassium bicarbonate is also mixed with the formamide, and this mixture is then added continuously to the toluene and acetaldehyde mixture. Preference is given to this order of addition.

In an alternative embodiment, the formamide and potassium carbonate mixture is added sequentially to the toluene and acetaldehyde mixture. The reaction time is generally between 0.5 hours and 10 hours, preferably between 1 and 7 hours.

The molar ratio between the acetaldehyde and the formamide generally ranges between 5:1 and 1:5, preferably between 2:1 and 1:2. The reaction temperature generally ranges between 0° and 40° C., preferably between 15° and 30° C.

The hydroxyethylformamide thus formed crystallizes and precipitates in the reaction medium. In order to control the crystallization, it is preferred to seed the toluene and acetaldehyde mixture with hydroxyethylformamide crystals, prior to adding the formamide and potassium bicarbonate mixture.

At the end of this first step, the hydroxyethylformamide crystals are separated from the solvent by a filtration step. In a non-limiting way, the filtration equipment can be a Nutsche filter, a filter press, a vertical or horizontal centrifuge, a rotary filter under vacuum or pressure, or simply a filter in the reactor if the latter is equipped at the drain with a grid with a suitable mesh to retain the hydroxyethylformamide crystals.

In a second step, methanol is added to the hydroxyethylformamide crystals. Methanol serves as both solvent and reagent in this step. The molar ratio between the methanol and the hydroxyethylformamide is generally between 20:1 and 1:2, preferably between 5:1 and 1:1.

The etherification reaction is catalyzed by an acid source, preferably a Brønsted acid. Any organic or inorganic acid source may be suitable, but preferentially sulfuric acid is chosen.

The sulfuric acid serves both to neutralize the residual potassium bicarbonate used in the first step, and as a reaction catalyst.

The reaction temperature is generally between 5 and 80° C., more preferentially between 10 and 40° C. The reaction time between hydroxyethylformamide and methanol is between 0.5 hours and 10 hours, more preferably between 1 and 8 hours. The reaction product is methoxyethylformamide in liquid form.

The methoxyethylformamide is subsequently purified to remove excess methanol and toluene. Preferentially, this purification is carried out by at least one vacuum distillation column.

In a third and final step, the methoxyethylformamide thus obtained undergoes a thermal decomposition reaction in the gas phase. The methoxyethylformamide is first heated in order to be vaporized. The methoxyethylformamide vapors are then introduced into the tubes of a pyrolyzer to undergo thermal decomposition. The tubes are heated to a temperature generally between 200 and 600° C., preferably between 250° and 550° C.

According to one embodiment the method is a method for obtaining N-vinylformamide by the alkoxy process, methanol being used as a protective agent, said method preferably comprising thermal decomposition of N-methoxyethylformamide at a temperature between 200° ° C. and 600° C. and at atmospheric pressure or under a partial vacuum.

The pyrolyzer may be operated at atmospheric pressure or under a partial vacuum, preferentially under a partial vacuum, more preferentially at an absolute pressure of less than 100 mbar.

The N-vinylformamide gases thus formed are generally cooled either by a condenser or by a gas scrubber supplied with pre-cooled liquid N-vinylformamide. The liquid thus obtained is a mixture of N-vinylformamide and methanol. An optional additional step is the evaporation of the methanol, such as on a falling film evaporator, flash evaporator, rotary evaporator or distillation column.

Monomer According to the Invention

The invention further relates to a bio-sourced-N-vinylformamide with a bio-sourced carbon content ranging between 5 wt % and 100 wt % relative to the total carbon mass in said N-vinylformamide, the bio-sourced carbon content being measured according to ASTM D6866-21 Method B. The same embodiments and preferences developed in the "method" section apply to this section of the monomer description.

The invention also relates to a bio-sourced-N-vinylformamide obtained by reaction between an acetaldehyde and a formamide, said acetaldehyde and/or said formamide, preferentially both, having a bio-sourced carbon content of between 5 wt % and 100 wt %, based on the total mass of carbon in said acetaldehyde and/or said formamide, respectively, wherein the bio-sourced carbon content is measured according to ASTM D6866-21 Method B.

Preferably, the acetaldehyde is totally renewable and non-fossil. Preferably, the formamide is totally renewable and non-fossil. Preferably, the acetaldehyde and the formamide are totally renewable and non-fossil.

In the whole invention, "Bio-sourced-N-vinylformamide" is understood to mean an N-vinylformamide that is at least partially, preferably totally derived from biomass, i.e. being the result of one or more chemical transformations carried out on one or more raw materials having a natural, and as opposed to non-fossil, origin. The bio-sourced-N-vinylformamide may also be referred to as bio-sourced or bio-resourced N-vinylformamide.

The acetaldehyde and/or the formamide, preferably both, can be non-segregated, partially segregated, or fully segregated. The preferences developed in the "method" section apply to this section describing the monomer.

In a particular embodiment, the acetaldehyde and/or the formamide, preferably both, may be partially or totally recycled. The preferences developed in the "method" section apply to this section describing the monomer.

In this particular embodiment, the monomer according to the invention is obtained by a method comprising the following steps:
Recycle at least one renewable and non-fossil raw material to obtain acetaldehyde and/or formamide;
React acetaldehyde and/or formamide to obtain an N-vinylformamide monomer.

Polymer According to the Invention

The invention relates to a polymer obtained by polymerization of at least one N-vinylformamide monomer obtained according to the method according to the invention. It also relates to a polymer obtained by polymerization of at least one N-vinylformamide monomer as previously described. The same embodiments and preferences developed in the "methods" section apply to this section The polymer according to the invention is preferably water-soluble or water-swellable. The polymer may also be a superabsorbent.

The polymer according to the invention may be a homopolymer or a copolymer with at least one N-vinylformamide monomer obtained according to the method according to the invention, or with at least one of the previously described N-vinylformamide monomers, and with at least one different additional monomer, the latter advantageously being chosen from at least one nonionic monomer, and/or at least one anionic monomer, and/or at least one cationic monomer, and/or at least one zwitterionic monomer, and/or at least one monomer comprising a hydrophobic grouping.

Thus, the copolymer may comprise at least a second monomer different from the first monomer (N-vinylformamide according to the invention), this second monomer being chosen from nonionic monomers, anionic monomers, cationic monomers, zwitterionic monomers, monomers comprising a hydrophobic grouping, and mixtures thereof.

The nonionic monomer is preferably selected from acrylamide, methacrylamide, N-isopropylacrylamide, N,N-dimethylacrylamide, N,N-diethylacrylamide, N-methylolacrylamide, N-vinylformamide (NVF), N-vinylacetamide, N-vinylpyridine and N-vinylpyrrolidone (NVP), N-vinyl imidazole, N-vinyl succinimide, acryloyl morpholine (ACMO), acryloyl chloride, glycidyl methacrylate, glyceryl methacrylate, and diacetone acrylamide.

The anionic monomer is preferably chosen from acrylic acid, methacrylic acid, itaconic acid, crotonic acid, maleic acid, fumaric acid, acrylamido undecanoic acid, 3-acrylamido 3-methylbutanoic acid, maleic anhydride, 2-acrylamido-2-methylpropane sulfonic acid (ATBS), vinylsulfonic acid, vinylphosphonic acid, allylsulfonic acid, methallylsulfonic acid, 2-sulfoethylmethacrylate, sulfopropylmethacrylate, sulfopropylacrylate, allylphosphonic acid, styrene sulfonic acid, 2-acrylamido-2-methylpropane disulfonic acid, and the water-soluble salts of these monomers, such as their alkali metal, alkaline earth metal or ammonium salts. It is preferably acrylic acid (and/or a salt thereof), and/or ATBS (and/or a salt thereof).

The cationic monomer is preferably chosen from quaternized dimethylaminoethyl acrylate (ADAME), quaternized dimethylaminoethyl methacrylate (MADAME), dimethyldiallylammonium chloride (DADMAC), acrylamido propyltrimethyl ammonium chloride (APTAC), and methacrylamido propyltrimethyl ammonium chloride (MAPTAC).

The zwitterionic monomer can be a derivative of a vinyl-type unit, particularly acrylamide, acrylic, allylic or maleic, this monomer having an amine or ammonium function (advantageously quaternary) and an acid function of the carboxylic (or carboxylate), sulfonic (or sulfonate) or phosphoric (or phosphate) type.

Monomers having a hydrophobic character can also be used in preparation of the polymer. Preferably, they are chosen from the group composed of esters of (meth)acrylic acid having an alkyl, arylalkyl, propoxylated, ethoxylated or ethoxylated and propoxylated chain; derivatives of (meth) acrylamide having an alkyl, arylalkyl, propoxylated, ethoxylated, ethoxylated and propoxylated chain, or dialkyl; alkyl aryl sulfonates, or of mono- or di-substituted amides of (meth)acrylamide having a propoxylated, ethoxylated, or ethoxylated and propoxylated alkyl, arylalkyl chain; derivatives of (meth)acrylamide having a propoxylated, ethoxylated, ethoxylated and propoxylated alkyl, arylalkyl, or dialkyl chain; alkyl aryl sulfonates Each of these monomers may also be bio-sourced.

According to the invention, the polymer may have a linear, branched, star, comb, dendritic or block structure. These structures can be obtained by selecting the initiator, the transfer agent, the polymerization technique such as controlled radical polymerization referred to as RAFT (reversible addition-fragmentation chain transfer), NMP (Nitroxide Mediated Polymerization) or ATRP (Atom Transfer Radical Polymerization), incorporation of structural monomers, the concentration . . . .

According to the invention, the polymer is advantageously linear and structured. A structured polymer refers to a non-linear polymer with side chains so as to obtain, when this polymer is dissolved in water, a pronounced state of entanglement leading to very substantial low gradient viscosities. The invention's polymer may also be cross-linked.

Additionally, the polymer according to the invention polymer may be structured:
By at least one structuring agent, which may be chosen from the group comprising polyethylenically unsaturated monomers (having at least two unsaturated functions), such as vinyl functions for example, particularly allyl, acrylic and epoxy functions, and one may mention, for example, methylene bis acrylamide (MBA), triallyamine, or tetraallylammonium chloride or 1,2 dihydroxyethylene bis-(N-acrylamide), and/or
By macroinitiators, such as polyperoxides, polyazoids and polytransfer agents, such as polymeric (co)polymers, and polyols, and/or
Functionalized polysaccharides.

The amount of branching/cross-linking agent in the monomer mixture is advantageously less than 4 wt % relative to the monomer content (weight), more advantageously less than 1%, and even more advantageously less than 0.5%. According to a particular embodiment, it may be at least equal to 0.00001 wt % relative to the monomer content.

In a particular embodiment, the polymer according to the invention may be a semi-synthetic and thus semi-natural polymer. In this embodiment, the polymer may be synthesized by copolymerization by total or partial grafting of at least one monomer according to the invention, and at least one natural compound, said natural compound being preferably chosen from starches and their derivatives, polysaccharides and their derivatives, fibers, vegetable gums, animal gums or algal gums, and modified versions thereof. For example, vegetable gums can include guar gum, gum arabic, locust bean gum, gum tragacanth, guanidinium gum, cyanine gum, tara gum, cassia gum, xanthan gum, ghatti gum, karaya gum, gellan gum, *Cyamopsis tetragonoloba* gum, soy gum, or beta-glucan or dammar. The natural compound can also be gelatin, casein, or chitosan. For example, algal gum can include sodium alginate or its acid, agar-agar, or carrageenan.

Polymerization is generally carried out, without this being limiting, by copolymerization or by grafting. The person skilled in the art will be able to refer to current general knowledge in the field of semi-natural polymers.

The invention also relates to a composition comprising at least one polymer according to the invention and at least one natural polymer, said natural polymer being preferably chosen from the previously described natural polymers. The weight ratio between the synthetic polymer and the natural polymer is generally between 90:10 and 10:90. The composition may be in liquid, inverse emulsion or powder form.

In general, the polymer does not require development of a particular polymerization method. Indeed, it can be obtained according to all the polymerization techniques well known to the person skilled in the art. In particular, it can be solution polymerization; gel polymerization; precipitation polymerization; emulsion polymerization (aqueous or inverse); suspension polymerization; reactive extrusion polymerization; water-in-water polymerization; or micellar polymerization.

Polymerization is generally free radical polymerization preferably by inverse emulsion polymerization or gel polymerization. Free radical polymerization includes free radical polymerization using UV, azo, redox or thermal initiators as well as controlled radical polymerization (CRP) techniques or matrix polymerization techniques.

The polymer according to the invention can be modified after it being obtained by polymerization. This is known as post-modification of the polymer. All known post-modifications can be applied to the polymer according to the invention, and the invention also relates to polymers obtained after said post-modifications. Among the possible post-modifications developed hereinafter, mention may be made of post-hydrolysis, post-modification by Mannich reaction, post-modification by Hoffman reaction and post-modification by glyoxalation reaction.

The polymer according to the invention can be obtained by performing a post-hydrolysis reaction on a polymer obtained by polymerization of at least one monomer obtained by the method according to the invention or at least one monomer as previously described in the "Monomer" section. Prior to post-hydrolysis, the polymer comprises acrylamide or methacrylamide monomer units, for example. The polymer may also further comprise monomeric units of N-Vinylformamide. More specifically, post-hydrolysis involves reaction of hydrolyzable functional groups of advantageously non-ionic monomeric units, more advantageously amide or ester functions, with a hydrolysis agent. This hydrolysis agent may be an enzyme, an ion exchange resin, an alkali metal, or a suitable acid compound. Preferably, the hydrolysis agent is a Brønsted base. Where the polymer comprises amide and/or ester monomer units, the post-hydrolysis reaction produces carboxylate groups. Where the polymer comprises vinylformamide monomer units, the post-hydrolysis reaction produces amine groups.

The polymer according to the invention can be obtained by performing a Mannich reaction on a polymer obtained by polymerization of at least one monomer obtained by the method according to the invention or at least one monomer as previously described in the "Monomer" section. More specifically, prior to the Mannich reaction, the polymer advantageously comprises acrylamide and/or methacrylamide monomer units. The Mannich reaction is performed in aqueous solution in the presence of a dialkyl amine and a formaldehyde precursor. More advantageously, the dialkyl amine is dimethylamine and the formaldehyde precursor is formaldehyde itself. After this reaction, the polymer contains tertiary amines.

The polymer according to the invention can be obtained by performing a Hoffman reaction on a polymer obtained by polymerization of at least one monomer obtained by the method according to the invention or at least one monomer as previously described in the "Monomer" section. Prior to the Hoffman reaction, the polymer advantageously comprises acrylamide and/or methacrylamide monomer units. The so-called Hofmann degradation reaction is carried out in aqueous solution in the presence of an alkaline earth and/or alkali hydroxide and an alkaline earth and/or alkali hypohalide.

Discovered by Hofmann at the end of the nineteenth century, this reaction is used to convert an amide function into a primary amine function with one carbon atom less. The detailed reaction mechanism is presented below.

In the presence of a Brønsted base (e.g., soda), a proton is extracted from the amide.

The amidate ion formed then reacts with the active chlorine ($Cl_2$) of the hypochlorite (e.g. NaClO which is in equilibrium: $2NaOH+Cl_2 \Leftrightarrow NaClO+NaCl+H_2O$) to produce an N-chloramide. The Brønsted base (e.g. NaOH) extracts a proton from the chloramide to form an anion. The anion loses a chloride ion to form a nitrene which undergoes isocyanate rearrangement.

By reaction between the hydroxide ion and the isocyanate, a carbamate is formed.

After decarboxylation (removal of $CO_2$) from the carbamate, a primary amine is obtained.

For the conversion of all or part of the amide functions of a (co)polymer comprising an amide group into an amine function, two main factors are involved (expressed in molar ratios). These are:
Alpha=(alkali and/or alkaline earth hypohalide/amide group) and
Beta=(alkali and/or alkaline earth hydroxide/alkali and/or alkaline earth hypohalide).

The polymer according to the invention can also be obtained by carrying out a glyoxalation reaction on a polymer obtained by polymerization of at least one monomer obtained by the method according to the invention or of at least one monomer as previously described in the "Monomer" section, said polymer comprising, with the glyoxalation reaction, at least one monomer unit advantageously of acrylamide or methacrylamide. More specifically, the glyoxalation reaction involves a reaction of at least one aldehyde on the polymer, thus allowing said polymer to be functionalized. Advantageously, the aldehyde may be chosen from the group comprising glyoxal, glutaraldehyde, furan dialdehyde, 2-hydroxyadipaldehyde, succinaldehyde, starch dialdehyde, 2.2 dimethoxyethanal, diepoxy compounds, and combinations thereof. Preferably, the aldehyde compound is glyoxal.

According to the invention, the polymer may be in liquid, gel or solid form when its preparation includes a drying step such as spray drying, drum drying, radiation drying, such as microwave drying, or fluid bed drying.

According to the invention, the water-soluble polymer preferably has a molecular weight between 1000 and 40 million g/mol. The polymer may be a dispersant, in which case its molecular weight is preferably between 1000 and 50,000 g/mol. The polymer may have a higher molecular weight, typically between 1 and 30 million g/mol. The molecular weight is understood as weight average molecular weight. The polymer according to the invention may also be a superabsorbent capable of absorbing from 10 to 500 times its weight in water.

The molecular weight is advantageously determined by the intrinsic viscosity of the (co)polymer. The intrinsic viscosity can be measured by methods known to the person skilled in the art and can be calculated from the reduced viscosity values for different (co)polymer concentrations by a graphical method entailing plotting the reduced viscosity values (y-axis) against the concentration (x-axis) and extrapolating the curve down to zero concentration. The intrinsic viscosity value is plotted on the y-axis or using the least squares method. The molecular weight can then be determined using the Mark-Houwink equation:

$$[\eta] = KM^\alpha$$

$[\eta]$ represents the intrinsic viscosity of the (co)polymer determined by the solution viscosity measurement method.
K represents an empirical constant.
M represents the molecular weight of the (co)polymer.
$\alpha$ represents the Mark-Houwink coefficient.
K and $\alpha$ depend on the specific (co)polymer-solvent system.

The co-monomers combined with the monomer according to the invention to obtain the polymer of the invention, are preferably at least partially, or more preferably totally renewable and non-fossil.

Thus, in a preferred embodiment, the invention relates to a polymer comprising:
  at least 5 mol %, preferably at least 10 mol %, preferably between 20 mol % and 99 mol %, more preferably between 30 mol % and 90 mol % of a first monomer, said monomer being a monomer according to the invention, and
  at least 1 mol %, preferably between 5 mol % and 90 mol %, more preferably between 10 mol % and 80 mol %, of at least one second monomer comprising ethylenic unsaturation, said second monomer being different from the first monomer, and being at least partially renewable and non-fossil.

Thus, in a preferred embodiment, the invention relates to a polymer comprising:
  at least 5 mol %, preferably at least 10 mol %, preferably between 20 mol % and 99 mol %, more preferably between 30 mol % and 90 mol % of a first monomer, said monomer being a monomer according to the invention; and
  at least 1 mol %, preferably between 5 mol % and 90 mol %, more preferably between 10 mol % and 80 mol %, of at least one second monomer comprising ethylenic unsaturation, said second monomer being different from the first monomer, and being at least partially renewable and non-fossil;
  at least 1 mol %, preferably between 5 mol % and 90 mol %, more preferably between 10 mol % and 80 mol % of at least one third monomer comprising an ethylenic unsaturation, said third monomer being different from the first and the second monomers, and being at least partially renewable and non-fossil.

The polymer according to the invention may comprise four or more different monomers.

In a preferred embodiment, the second and the possible other monomers have a bio-sourced carbon content ranging between 5 wt % and 100 wt %, preferably 10 wt % and 100 wt %, relative to the total carbon weight in the related monomer, the bio-sourced carbon content being measured according to ASTM D6866-21 Method B.

In a preferred embodiment according to the invention, the second monomer and any other monomers are chosen from acrylamide, (meth)acrylic acid and/or a salt thereof, 2-acrylamido-2-methylpropane sulfonic acid (ATBS) and/or a salt thereof, N-vinylpyrrolidone (NVP) dimethylaminoethyl (meth)acrylate and quaternized versions thereof, dimethyldiallylammonium chloride (DADMAC), a substituted acrylamide with the formula $CH_2=CHCO-NR^1R^2$, $R^1$ and $R^2$ being, independently of each other, a linear or branched carbon chain $C_nH_{2n+1}$, wherein n ranges between 1 and 10.

In the whole invention, it will be understood that the molar percentage of the monomers (excluding any crosslinking agents) of the polymer is equal to 100%.

The invention also relates to a polymer obtained by polymerization of at least one N-vinylformamide monomer obtained according to the method according to the invention, or of at least one N-vinylformamide monomer previously described, said polymer then being partially or totally hydrolyzed by acid or basic hydrolysis, in order to convert at least one N-vinylformamide monomer unit into N-vinylamine.

In this embodiment, the polymer before hydrolysis is a polymer preferentially comprising at least 80 mol % of N-vinylformamide monomer unit. Preferentially, it is a N-vinylformamide homopolymer. The hydrolysis rate may range between 20 and 100%, preferably between 25 and 90%, even more preferably between 30 and 80%, this rate representing the percentage of N-vinylformamide monomer unit converted into vinylamine monomer unit relative to the total number of N-vinylformamide monomer units present in the polymer before hydrolysis.

In this embodiment, the hydrolysis is preferentially carried out on a N-vinylformamide homopolymer. The polymer obtained after hydrolysis is a vinylformamide/vinylamine copolymer or a vinylamine homopolymer. The molar percentage of vinylamine units of said polymer (or homopolymer) preferentially ranges between 20 and 100%, preferably between 25 and 90%, even more preferably between 30 and 80%.

Preferably, the polymer according to the invention comprises a bio-sourced carbon content ranging between 5 wt % and 100 wt % relative to the total carbon mass in said polymer, the bio-sourced carbon content being measured according to ASTM D6866-21 Method B.

The invention also relates to the use of at least one N-vinylformamide monomer obtained by the method according to the invention, or previously described, in order to synthesize a polymer.

Using the Polymer According to the Invention

The invention also relates to the use of the polymer according to the invention in the recovery of hydrocarbons (oil and/or gas); in drilling and cementing of wells; in the stimulation of hydrocarbon wells (oil and/or gas), for example hydraulic fracturing, conformation, diversion; in the treatment of water in open, closed or semi-closed circuits; in the treatment of fermentation slurry, treatment of sludge; in paper manufacturing; in construction; in wood processing; in hydraulic composition processing (concrete, cement, mortar and aggregates); in the mining industry; in the formulation of cosmetic products; in the formulation of detergents; in textile manufacturing; in battery component manufacturing; in geothermal energy; in sanitary napkin manufacturing; or in agriculture.

The invention also relates to the use of the polymer according to the invention as a flocculant, coagulant, binding agent, fixing agent, viscosity reducing agent, thickening agent, absorbing agent, friction reducing agent, dewatering agent, draining agent, charge retention agent, dehydrating agent, conditioning agent, stabilizing agent, film forming agent, sizing agent, superplasticizing agent, clay inhibitor or dispersant.

Method Using the Polymer According to the Invention

The present invention also relates to the various methods described hereinafter, wherein the polymers of the invention are used to improve application performance.

The invention also relates to a method for enhanced oil or gas recovery by sweeping a subterranean formation comprising the following steps:
  a. Preparing an injection fluid from a polymer according to the invention with water or brine,
  b. Injecting the injection fluid into a subterranean formation,
  c. Sweeping the subterranean formation with the injected fluid,
  d. Recovering an aqueous mixture of oil and/or gas.

The invention also relates to a method for hydraulic fracturing of subterranean oil and/or gas reservoirs comprising the following steps:
  a. Preparing an injection fluid from a polymer according to the invention, with water or brine, and with at least one proppant,
  b. Injecting said fluid into the subterranean reservoir and fracturing at least a portion thereof to recover oil and/or gas.

In the methods described hereinabove, the polymer is preferably a high molecular weight polymer (greater than 8 million daltons). It is preferably linear. It is preferably in the form of a powder, an inverse emulsion, a partially dehydrated inverse emulsion, or in the form of a "clear", i.e. a dispersion of solid polymer particles in an aqueous or oily fluid. The powder form is preferably obtained by gel or spray drying of an inverse emulsion. It also involves a composition comprising an inverse emulsion of a polymer according to the invention and solid particles of a polymer according to the invention.

The invention also relates to a method of stimulation of a subterranean formation comprising the following steps:
  a. Preparing an injection fluid from a polymer according to the invention with water or brine,
  b. Injecting the injection fluid into a subterranean formation,
  c. Partially or totally plugging the subterranean formation with the injected fluid, said plugging being temporary or permanent.

The invention also related a method of drilling and/or cementing a well in a subterranean formation comprising the following steps:
  a. Preparing an injection fluid from a polymer according to the invention with water or brine,
  b. Injecting said drilling and/or cementing fluid into the subterranean formation via the drill head in at least one step of drilling or cementing a well.

Drilling and cementing a well are two successive steps in creating a well in a subterranean formation. The first step is drilling with the drilling fluid, while the second step is cementing the well with the cementing fluid. The invention also relates to a method of injecting an intermediate fluid ("spacer fluid") injected between the drilling fluid and the cementing fluid, said intermediate fluid comprising at least one polymer according to the invention. This intermediate fluid prevents contamination between the cementing fluid and the drilling fluid.

When drilling and cementing a well, the polymer according to the invention can be used as a fluid loss additive in well cement compositions in order to reduce fluid loss from the cement compositions to permeable formations or zones into or through which the cement compositions are pumped. In primary cementing, loss of fluid, i.e., water, to permeable formations or subterranean zones can lead to premature gelling of the cement composition, so that bridging the annular space between the permeable formation or zone and the drill string cemented therein prevents the cement composition from being placed along the entire length of the ring.

The invention also relates to a method of inerting clays in hydraulic compositions for construction purposes, said method comprising a step of adding to the hydraulic composition or one of its constituents at least one clay inerting agent, characterized in that the clay inerting agent is a polymer according to the invention.

Clays can absorb water and cause poor performance of building materials. When the polymer of the invention is used as a clay inhibitor, it allows in particular to avoid the clay swelling which may cause cracks thus weakening any building.

The hydraulic composition may be a concrete, cement, mortar or aggregate. The polymer is added to the hydraulic composition or to one of its constituents advantageously at a dosage of 2 to 200 ppm of inerting agent relative to the weight of aggregate.

In this method of inerting clays, clays include, but are not limited to, 2:1 swelling clays (such as smectite), or 1:1 swelling clays (such as kaolin) or 2:1:1 swelling clays (such as chlorite). The term "clay" generally refers to magnesium and/or aluminum silicate, including phyllo silicates with a lamellar structure. However, in the present invention, the term "clay" also includes clays having no such structure, such as amorphous clays.

The invention also relates to a method for manufacturing a sheet of paper, cardboard or the like, whereby, before a sheet is formed, a step is performed entailing adding to a suspension of fibers, at one or more injection points, at least one polymer according to the invention. The polymer may provide dry strength or retention properties or wet strength. It may also improve paper formation, drainage and dewatering capabilities.

The method can be used successfully to manufacture packaging papers and cardboards, coating papers, sanitary and household papers, any type of paper, cardboard or the like.

The post-modified polymers described in the "Polymers" section, in particular the post-modified polymers by Hoffman reaction or by glyoxalation reaction, are particularly advantageous in methods for manufacturing paper, cardboard or the like.

Retention properties are understood to mean the capability to retain the suspended materials of the paper pulp (fibers, fines, fillers (calcium carbonate, titanium oxide), . . . ) on the forming fabric, thus in the fibrous mat that will make up the final sheet. The mode of action of the retention agents is based on the flocculation of these suspended materials in water. Indeed, the flocs formed are more easily retained on the forming sheet.

The retention of fillers involves retaining specifically the fillers (small mineral species with little affinity with cellulose). Substantial improvement of retention of fillers leads to a clarification of white water by retaining the fillers in the sheet and by increasing its grammage. It also gives the possibility to replace part of the fibers (the most expensive species in the composition of paper, cardboard or similar) with fillers (lower costs) in order to reduce manufacturing costs.

As concerns dewatering (or drainage) properties, it is the capacity of the fibrous mat to evacuate or drain the maximum amount of water so that the sheet dries as quickly as possible, in particular during manufacturing of the sheet.

These two properties (retention and drainage) being intricately linked, one depending on the other, the issue is therefore to find the best compromise between retention and drainage. Generally, the person skilled in the art refers to a retention and drainage agent because these are the same types of products used to improve these two properties.

Fibrous suspension is understood to mean thick pulp or diluted pulp which are composed of water and cellulose fibers. The thick stock, with a dry matter concentration of more than 1% or even more than 3%, is located upstream of the fan pump. The thin stock, with a dry mass concentration of generally less than 1%, is located downstream of the fan pump.

The polymer can be added to the thick stock or to the thin stock. It can be added at the level of the fan pump or the headbox. Preferably, the polymer is added before the headbox.

In the method for making paper, cardboard or the like according to the invention, the polymer according to the invention may be used alone or in combination with a secondary retention agent. Preferably, a secondary retention agent selected from organic polymers and/or inorganic microparticles is added to the fiber suspension.

This secondary retention agent added to the fibrous suspension is advantageously chosen from anionic polymers in the broad sense, which can therefore be (without being limiting) linear, branched, cross-linked, hydrophobic, associative and/or inorganic microparticles (such as bentonite, colloidal silica).

The invention also relates to a method for treating a suspension of solid particles in water resulting from mining or oil sands operations, comprising contacting said suspension with at least one polymer according to the invention. Such a method can be carried out in a thickener, which is a holding zone, generally in the form of a tube section of several meters in diameter with a conical bottom wherein the particles can settle. According to a specific embodiment, the aqueous suspension is transported by means of a pipe to a thickener, and the polymer is added to said pipe.

According to another embodiment, the polymer is added to a thickener that already contains the suspension to be treated. In a typical mineral processing operation, the suspensions are often concentrated in a thickener. This results in a higher density sludge that exits the bottom of the thickener, and an aqueous fluid released from the treated suspension (called liquor) that exits by overflow, from the top of the thickener. Generally, the addition of the polymer increases the concentration of the sludge and increases the clarity of the liquor.

According to another embodiment, the polymer is added to the particulate suspension during transport of said suspension to a deposition area. Preferably, the polymer is added in the pipe that conveys said suspension to a deposition zone. It is on this deposition area that the treated suspension is spread in preparation for dewatering and solidification. The deposition areas can be either open, such as an unconfined area of soil, or enclosed, such as a basin, cell.

An example of such treatments during transport of the suspension is spreading the suspension treated with the polymer according to the invention on the soil in preparation for dewatering and solidification and then spreading a second layer of treated suspension on top of the solidified first layer. Another example is the continuous spreading of the suspension treated with the polymer according to the invention in such a way that the treated suspension falls continuously on the suspension previously discharged in the deposition area, thus forming a mass of treated material from which water is extracted.

According to another embodiment, the water-soluble polymer is added to the suspension and a mechanical treatment is performed, such as centrifugation, pressing or filtration.

The water-soluble polymer can be added simultaneously in different stages of the suspension treatment, i.e., for example, in the pipe carrying the suspension to a thickener and in the sludge exiting the thickener which will be conveyed either to a deposition area or to a mechanical treatment device.

The invention also relates to a method for treating municipal or industrial water, comprising the introduction into said water to be treated of at least one polymer according to the invention. Effective water treatment requires the removal of dissolved compounds, and dispersed and suspended solids from the water. Generally, this treatment is enhanced by chemicals such as coagulants and flocculants. These are usually added to the water stream ahead of the separation unit, such as flotation and sedimentation.

The polymers according to the invention can be advantageously used to coagulate or flocculate suspended particles in municipal or industrial wastewater. Generally, they are used in combination with inorganic coagulants such as alum.

They can also be used advantageously to treat the sludge produced from the treatment of this wastewater. Sewage sludge (be it urban or industrial) is the main waste produced by a treatment plant from liquid effluents. Generally, sludge treatment involves dewatering it. This dewatering can be performed by centrifugation, filter press, belt press, electrodewatering, sludge drying reed beds, solar drying. It is used to decrease sludge water concentration.

In this municipal or industrial water treatment process, the polymer according to the invention is preferably linear or branched. It is preferably in the form of a powder, an inverse emulsion or a partially dehydrated inverse emulsion. The powder form is preferably obtained by gel or spray drying from an inverse emulsion.

The invention also relates to an additive for a cosmetic, dermatological or pharmaceutical composition, said additive comprising at least one polymer according to the invention. The invention also relates to the use of the polymer according to the invention in manufacturing said compositions as a thickening (agent), conditioning (agent), stabilizing (agent), emulsifying (agent), fixing (agent) or film-forming agent. The invention equally relates to cosmetic, dermatological or pharmaceutical compositions comprising at least one polymer according to the invention.

In particular, reference may be made to application FR2979821 on behalf of L'OREAL for the manufacture of such compositions and description of the other ingredients of such compositions. The said compositions may be in the form of a milk, a lotion, a gel, a cream, a gel cream, a soap, a bubble bath, a balm, a shampoo or a conditioner. The use of said compositions for the cosmetic or dermatological treatment of keratinous materials, such as the skin, scalp, eyelashes, eyebrows, nails, hair and/or mucous membranes is also an integral part of the invention. Such use comprises application of the composition to the keratinous materials, possibly followed by rinsing with water.

The invention also relates to an additive for detergent composition, said additive comprising at least one polymer according to the invention. The invention also relates to the use of the polymer according to the invention in manufacturing said compositions as a thickening (agent), conditioning (agent), stabilizing (agent), emulsifying (agent), fixing (agent) or film-forming (agent). The invention equally relates to detergent compositions for household or industrial use comprising at least one polymer according to the invention. In particular, reference may be made to the applicant's application WO2016020622 for the manufacture of such compositions and description of the other ingredients of such compositions.

"Detergent compositions for household or industrial use" are understood to mean compositions for cleaning various surfaces, particularly textile fibers, hard surfaces of any kind such as dishes, floors, windows, wood, metal or composite surfaces. Such compositions include, for example, detergents for washing clothes manually or in a washing machine, products for cleaning dishes manually or for dishwashers, detergent products for washing house interiors such as kitchen elements, toilets, furnishings, floors, windows, and other cleaning products for universal use.

The polymer used as an additive, e.g., thickener, for a cosmetic, dermatological, pharmaceutical, or detergent composition is preferably cross-linked. It is preferably in the form of a powder, an inverse emulsion or a partially dehydrated inverse emulsion. The powder form is preferably obtained by spray drying from an inverse emulsion.

The invention equally relates to a thickener for pigment composition used in textile printing, said thickener comprising at least one polymer according to the invention. The invention also relates to a textile fiber sizing agent, said agent comprising at least one polymer according to the invention.

The invention also relates to a process for manufacturing superabsorbent from the monomer according to the invention, a superabsorbent obtained from at least one monomer according to the invention, said superabsorbent to be used for absorbing and retaining water in agricultural applications or for absorbing aqueous liquids in sanitary napkins. For example, the superabsorbent agent is a polymer according to the invention.

The invention also relates to a method for manufacturing sanitary napkins wherein a polymer according to the invention is used, for example as a superabsorbent agent.

The invention also relates to the use of the polymer according to the invention as a battery binder. The invention also relates to a battery binder composition comprising the polymer according to the invention, an electrode material and a solvent. The invention also relates to a method for manufacturing a battery comprising making a gel comprising at least one polymer according to the invention and filling same into said battery. Mention may be made of lithium ion batteries which are used in a variety of products, including medical devices, electric cars, aircraft and, most importantly, consumer products such as laptops, cell phones and cameras.

Generally, lithium ion batteries (LIBs) include an anode, a cathode, and an electrolyte material such as an organic solvent containing a lithium salt. More specifically, the anode and cathode (collectively, the "electrodes") are formed by mixing an electrode active material (anode or cathode) with a binder and solvent to form a paste or sludge that is then applied and dried onto a current collector, such as aluminum or copper, to form a film on the current collector. The anode and cathode are then stacked and wound before being housed in a pressurized case containing an electrolyte material, all of which together form a lithium-ion battery.

In a lithium battery, the binder plays several important roles in both mechanical and electrochemical performance. Firstly, it helps disperse the other components in the solvent during the manufacturing process (some also act as a thickener), thus allowing for even distribution. Secondly, it holds the various components together, including the active components, any conductive additives, and the current collector, ensuring that all of these parts stay in contact. Through chemical or physical interactions, the binder connects these separate components, holding them together and ensuring the mechanical integrity of the electrode without a material impact on electronic or ionic conductivity. Thirdly, it often serves as an interface between the electrode and the electrolyte. In this role, it can protect the electrode from corrosion or the electrolyte from depletion while facilitating ion transfer across this interface.

Another important point is that the binders must have a certain degree of flexibility so that they do not crack or develop defects. Brittleness can create problems during manufacturing or assembly of the battery.

Given all the roles it plays in an electrode (and in the battery as a whole), choosing a binder is critical in ensuring good battery performance.

The invention also relates to a method for manufacturing sanitary napkins wherein a polymer according to the invention is used, for example as a superabsorbent agent.

As previously described, the circular economy is an economic system devoted to efficiency and sustainability that minimizes waste by optimizing value generated by resources. It relies heavily on a variety of conservation and recycling practices in order to break away from the current more linear "take-make-dispose" approach.

Therefore, with material recycling being a major and growing concern, recycling processes are developing rapidly and enabling the production of materials that can be used to produce new compounds or objects. Recycling materials does not depend on the origin of the material and as long as it can be recycled, it is considered as a technical progress. Although the origin of the material to be recycled may be renewable and non-fossil, it may also be fossil.

Specific objects are described hereinafter.

A method for obtaining N-vinylformamide comprises the reaction between an acetaldehyde and a formamide, one of the two, preferentially both, being derived at least partially, preferentially totally, from a recycling process of a renewable and non-fossil material, or from a fossil material.

Preferentially, the acetaldehyde and/or the formamide, preferentially both, are totally "segregated", i.e., from a separate pipeline and treated separately. In an alternative embodiment, it is (they are) partially "segregated" and partially "non-segregated". In this case, the weight ratio between the "segregated" part and the "non-segregated" part is preferentially between 99:1 and 25:75, preferably between 99:1 and 50:50. In an alternative embodiment, it is (they are) totally "non-segregated".

An N-vinylformamide may be obtained by reaction between an acetaldehyde and a formamide, said acetaldehyde and/or said formamide, preferentially both, being derived at least partially, preferentially totally, from a recycling process of a renewable and non-fossil material, or from a fossil material.

A polymer obtained by polymerization of at least one N-vinylformamide monomer as just previously described.

A use of a polymer obtained by polymerization of at least one N-vinylformamide monomer as just previously described, in the oil and/or gas recovery, in drilling and cementing of wells; in the stimulation of oil and/or gas wells (for example hydraulic fracturing, conformation, diversion), in the treatment of water in open, closed or semi-closed circuits, in the treatment of fermentation slurry, treatment of sludge, in paper manufacturing, in construction, in wood processing, in hydraulic composition processing (concrete, cement, mortar and aggregates), in the mining industry, in the formulation of cosmetic products, in the formulation of detergents, in textile manufacturing, in battery component manufacturing; in geothermal energy; or in agriculture.

A use of a polymer obtained by polymerization of at least one N-vinylformamide monomer as just previously described as a flocculant, coagulant, binding agent, fixing agent, viscosity reducing agent, thickening agent, absorbing agent, friction reducing agent, dewatering agent, draining agent, charge retention agent, dehydrating agent, conditioning agent, stabilizing agent, film forming agent, sizing agent, superplasticizing agent, clay inhibitor or dispersant.

A polymer obtained according to a method comprising the following steps:

Recycling at least one renewable and non-fossil, or a fossil raw material to obtain acetaldehyde and/or formamide;

Reacting said acetaldehyde with said formamide to obtain N-vinylformamide;

Polymerizing said N-vinylformamide with optionally another ethylenically unsaturated monomer.

EXAMPLES

Figure 1:
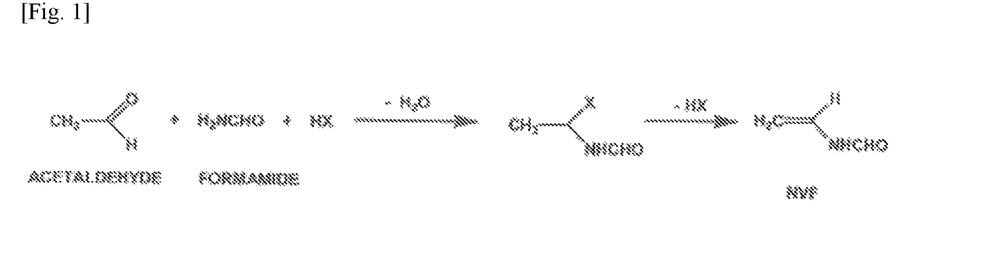
FIG. 1 shows NVF formation from acetaldehyde and formamide.

The following examples relate to the synthesis of a bio-sourced N-vinylformamide according to the invention (hereinafter abbreviated NVF), comprising the reaction between an acetaldehyde (hereinafter abbreviated ACH), and a formamide (hereinafter abbreviated FAM), one of the two, preferably both, being at least partly of renewable and non-fossil origin (see FIG. 1). They also relate to the synthesis and the use of a bio-sourced polymer obtained from at least one bio-sourced N-vinylformamide monomer according to the invention.

The following examples serve to best illustrate the advantages of the invention.

Description of Purity Test.

The synthesis of NVF takes place in two steps, with first obtaining hydroxyethylformamide from acetaldehyde and formamide. The hydroxyethylformamide is then transformed into methoxyethylformamide (hereinafter abbreviated MEF) by reaction with methanol and a catalyst. The methoxyethylformamide is then pyrolyzed at high temperature in order to obtain N-vinylformamide.

The purity of the NVF is determined by high performance liquid chromatography, according to the following analysis conditions (Table 2):

TABLE 2

| | |
|---|---|
| Mobile phase gradient | From 0 to 9 minutes: 99% water weight + 1% acetonitrile weight<br>From 9 to 17 minutes: 80% water weight + 20% acetonitrile weight |
| Injection volume | 10 μL |
| Column temperature | 40° C. |
| Injection rate | 0.5 mL/min |
| Detection wavelength | 200 nm |
| Analysis time: | 17 minutes |
| Features of the HPLC column | Column filled with $C_{18}$ silica, Zorbax Eclipse Plus C18 RRHT type, with a diameter of 3 mm. a length of 150 mm, and containing particles having a size of 1.8 μm |

Using these conditions, and by measuring the areas of the various impurity peaks, the purity of NVF can be calculated.

The quantification of formamide and methoxyethylformamide is carried out via a calibration of standards.

The retention time of formamide is 1.43 minutes and that of methoxyethylformamide is 4.5 minutes.

I. Synthesis of Partially Bio-Sourced NVF

Example 1: Synthesis of NVF with FAM Partly of Renewable and Non-Fossil Origin and ACH of Fossil Origin A set of tests was carried out by varying the origin of the formamide and its percentage in $^{14}C$: FAM of fossil origin CE 1 and FAM partly of renewable and non-fossil origin Inv 1 to Inv 7 (Table 3).

The levels of $^{14}C$ are measured according to the ASTM D6866-21 standard, method B. This standard makes it possible to characterize the bio-sourced nature of a chemical compound by determining the bio-sourced carbon level of said compound.

A "zero" wt % $^{14}C$ represents the total absence of measurable $^{14}C$ in a material, thus indicating a fossil carbon source.

As indicated in Table 3, formamide of non-fossil origin comes from various sources, such as the treatment of residues from the paper pulp industry ("tall oil"), or agricultural waste in order to form the precursor formic acid (via bio-methanol) or ethyl formate (via bio-ethane), or from the treatment of municipal waste, biomass, or fermentation or recycling of carbon dioxide, or even the amino portion of formamide can be derived from green ammonia.

The procedure was carried out as follows for each test: 800 g of toluene are added to a 2 000 mL reactor equipped with a jacket, a stirrer and a condenser.

The reactor is degassed with nitrogen in order to drive out the air present therein.

The reactor is maintained at a temperature of 20° C., in order to be able to introduce 235 g of acetaldehyde therein.

A casting funnel is loaded with 200 g of formamide containing 1.33 g of potassium bicarbonate.

20% of the contents of the dropping funnel feeds the reactor over a period of 30 minutes, while maintaining the reaction medium at 20° ° C., 0.5 g of hydroxyethylformamide crystals are then added to the reaction medium as crystallization seed. After a waiting time of 30 minutes, the remaining quantity of formamide and potassium bicarbonate contained in the dropping funnel are added to the reaction medium for a period of 3 hours. The temperature is maintained at 20° C. throughout the reaction in order to prevent the loss of acetaldehyde by evaporation.

The hydroxyethylformamide obtained is a white solid suspended in toluene, which is separated by Buchner filtration. The solid obtained is again introduced into the reactor and then 430 g of methanol and 3.5 g of 98% concentrated sulfuric acid in water are added. The mixture is heated at a temperature of 25° C. for 2 hours. At the end of this reaction, 20% sodium hydroxide is added in order to neutralize the acidity of the medium induced by the sulfuric acid. Sulfate salts are separated by filtration.

The liquid obtained is composed of methoxyethylformamide, toluene, methanol and by-products. The reactor condenser is replaced by a 20 cm high glass column filled with Propack type packing. The whole is placed under a vacuum of 10 mbar (1 bar=0.1 MPa) and the reactor heated to 60° C. The light product fractions are discarded and only the fraction corresponding to pure methoxyethylformamide is retained.

A pyrolyzer is equipped with a tube of 10 mm in diameter and a length of 20 cm, and heated by an external electrical resistance. The methoxyethylformamide is loaded into a jacketed reactor which is connected for the gas phase to the inlet of the pyrolyzer. A 5° glycol water condenser is connected to the outlet of the pyrolyser. The whole is placed under a vacuum of 90 mbar, the pyrolyser being heated to a temperature of 430° C. The jacketed reactor is heated to a temperature of 150° C. in order to vaporize the methoxyethylformamide.

The pyrolysis gases are cooled by the condenser and collected in a glass flask. The liquid obtained is distilled with a rotary evaporator under a reduced vacuum in order to eliminate the methanol. The remaining N-vinylformamide in the flask is weighed to determine the yield of the reaction relative to the starting formamide, and is analysed by liquid chromatography to determine the content of formamide and methoxyethylformamide impurities.

TABLE 3

| | Origin FAM | wt % $^{14}C$ of FAM | % FAM conversion | FAM in NVF obtained (%) | MEF in obtained NVF (%) |
|---|---|---|---|---|---|
| CE 1 | Fossil | 0 | 78 | 2.6 | 4.2 |
| Inv 1 | Bio-ethane (agricultural waste) | 40 | 79 | 2.2 | 3.7 |
| Inv 2 | $CO_2$ capture + Green ammonia | 40 | 79 | 2.1 | 3.8 |

TABLE 3-continued

| | Origin FAM | wt % $^{14}C$ of FAM | % FAM conversion | FAM in NVF obtained (%) | MEF in obtained NVF (%) |
|---|---|---|---|---|---|
| Inv 3 | $CO_2$ capture + Green ammonia | 50 | 81 | 2 | 3.7 |
| Inv 4 | Bio-methanol (agricultural waste) | 50 | 80 | 2.2 | 3.8 |
| Inv 5 | Bio-methanol (biomass) + Green ammonia | 70 | 82 | 1.9 | 3 |
| Inv 6 | Bio-methanol (biomass) + Green ammonia | 80 | 84 | 1.6 | 2.9 |
| Inv 7 | Bio-methanol (agricultural waste) + Green ammonia | 100 | 86 | 1.4 | 1.8 |

(CE = counter-example; Inv = example according to the invention)

The Applicant has observed that the bio-sourced nature of formamide allows better conversion, and generates fewer impurities.

Example 2: Synthesis of NVF with Fossil-Based FAM and Partly Renewable and Non-Fossil ACH A set of tests was carried out according to the protocol previously described by adjusting the origin of the ACH and its percentage of $^{14}C$: ACH of fossil origin CE 2 and ACH partly of renewable and non-fossil origin Inv 8 to Inv 14 (Table 4).

Acetaldehyde of non-fossil origin comes from the treatment of residues from the paper pulp industry ("tall oil"), or from agricultural waste in order to form the bioethanol or bio-ethane precursor, or from the of treatment municipal waste, biomass, or carbon dioxide fermentation or recycling.

The rate of $^{14}C$ in the various ACH is measured, as previously, according to standard ASTM D6866-21 method B.

TABLE 4

| | ACH origin | wt % $^{14}C$ of FAM | % FAM conversion | FAM in NVF obtained (%) | MEF in obtained NVF (%) |
|---|---|---|---|---|---|
| CE 2 | Fossil | 0 | 77 | 2.5 | 4.1 |
| Inv 8 | Bioethane (biomass) | 40 | 78 | 2.1 | 3.8 |
| Inv 9 | Bioethane (biomass) | 50 | 81 | 1.9 | 3.6 |
| Inv 10 | Bioethanol (agricultural waste) | 40 | 79 | 2.3 | 3.8 |
| Inv 11 | Bioethanol (agricultural waste) | 50 | 81 | 2 | 3.5 |
| Inv 12 | Bioethanol (agricultural waste) | 70 | 82 | 1.6 | 2.8 |
| Inv 13 | Bioethanol (agricultural waste) | 80 | 83.5 | 1.3 | 2.5 |
| Inv 14 | Bioethanol (agricultural waste) | 100 | 87 | 1.2 | 1.7 |

(CE = counter-example; Inv = example according to the invention)

The applicant has observed that the percentage of conversion of FAM is greater when the ACH is at least partly of renewable and non-fossil origin.

Example 3: Synthesis of NVF Used According to the Invention

A set of tests was carried out according to the protocol previously described by adjusting the origin of the FAM and the ACH (cf examples 1 and 2) and their percentages of $^{14}$C: comparative monomer CE 3 and monomers according to the invention M1 to M7 (Table 5).

TABLE 5

| Monomers | CE 3 | M1 | M2 | M3 | M4 | M5 | M6 | M7 |
|---|---|---|---|---|---|---|---|---|
| FAM origin | CE 1 | Inv 2 | Inv 3 | Inv 1 | Inv 4 | Inv 5 | Inv 6 | Inv 7 |
| ACH origin | CE 2 | Inv 8 | Inv 9 | Inv 10 | Inv 11 | Inv 12 | Inv 13 | Inv 14 |
| % FAM conversion | 78 | 80 | 82 | 79 | 80 | 82 | 85 | 88 |
| FAM in NVF obtained (%) | 2.5 | 2 | 1.9 | 2.1 | 2 | 1.5 | 1 | 0.9 |
| MEF in the NVF obtained (%) | 4 | 3.7 | 3.6 | 3.5 | 3.7 | 2.1 | 1.8 | 1.2 |

(CE = counter-example; Inv = example according to the invention)

The applicant observes that the use of FAM partially or totally of renewable and non-fossil origin, and of ACH partially or totally of renewable and non-fossil origin, according to the invention, makes it possible to optimize the process for obtaining NVF.

II. Synthesis and Use of Bio-Sourced Polymer According to the Invention:

Example 4: Synthesis and Biodegradability of Polymers P1 to P4 According to the Invention and of a Comparative Polymer CE 4 (Table 6)

350 g of deionised water is added to a 1 000 mL jacketed reactor, equipped with a condenser and a stirrer.

The pH is adjusted to 6.5 by adding 75% phosphoric acid diluted in water or 20% sodium hydroxide diluted in water.

The solution thus obtained is heated to 80° C., bubbling with nitrogen is carried out for 30 minutes in order to eliminate all traces of dissolved oxygen.

The following are then added to the reactor:
120 g of N-vinylformamide obtained according to one of the preceding examples are added continuously for 120 minutes.
Concomitantly, 0.54 g of 2,2'-Azobis(2-methylpropionamidine) dihydrochloride dissolved in 7 g of water is also added continuously for 180 minutes.

After the addition of the above reagents, the reaction medium is maintained at 80° C for 60 minutes. A viscous liquid is then obtained.

20 g of sodium bisulphite at 40% concentration, followed by 295 g of 25% sodium hydroxide are then added to the reaction medium (wt % in water).

The hydrolysis of the polymer is thus carried out for 300 minutes at 80° C.

The product obtained is cooled to 30° C. then 130 g of 22% concentrated hydrochloric acid in water are added to neutralize the excess sodium hydroxide.

The biodegradability (after 28 days) of the polymers obtained is evaluated according to the OECD 302B standard (Table 6).

TABLE 6

| Polymer | P1 | P2 | P3 | P4 | CE4 |
|---|---|---|---|---|---|
| Mass of NVF (g) | 120 | 120 | 120 | 120 | 120 |
| Monomers | Inv 7 CE 2 | CE 1 Inv 14 | M7 | M6 | CE 3 |
| wt % $^{14}$C of FAM | 100 | 0 | 100 | 80 | 0 |

TABLE 6-continued

| Polymer | P1 | P2 | P3 | P4 | CE4 |
|---|---|---|---|---|---|
| wt % $^{14}$C of ACH | 0 | 100 | 100 | 80 | 0 |
| wt % $^{14}$C of NVF | 33 | 67 | 100 | 80 | 0 |
| % biodegradability | 15 | 26 | 40 | 33 | 5 |

(CE = counter-example)

The polymers P1 to P4 according to the invention, obtained from partially or totally bio-sourced monomers are more easily biodegradable than the polymer CE 4 obtained from fossil monomers.

Example 5: Use of a Polymer According to the Invention as an Additive in a Papermaking Process Retention agents are polymers added to cellulose fibre pulps prior to paper formation to increase the retention efficiency of the paper.

Types of Pulp Used: Recycled Fiber Pulp

The wet pulp is obtained by disintegrating dry pulp in order to obtain a final aqueous concentration of 1 wt %. It is a pH-neutral pulp made from 100% recycled cardboard fibres.

A/Evaluation of Drainage Performance (DDA)

The DDA ("Dynamic Drainage Analyzer") makes it possible to automatically determine the time (in seconds) required to drain a fibrous suspension under vacuum. The polymers are added to the wet pulp (0.6 liters of pulp at 1.0 wt %) in the cylinder of the DDA at 1000 rpm (revolutions per minute):
T=0 s: stirring the pulp
T=20 s: Addition of polymer
T=30 s: stirring stopped and draining under vacuum at 200 mbar for 70 seconds.

Figure 2:
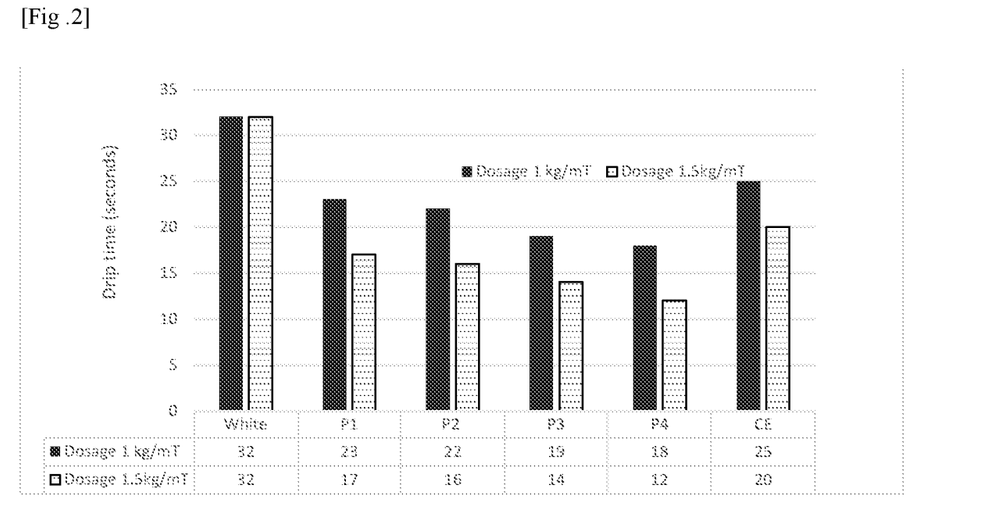
FIG. 2 shows vacuum drainage performance at 1 kg/mt and 1.5 kg/mt.

The pressure under the canvas is recorded as a function of time. When all the water is evacuated from the fibrous mat, the air passes through it causing a break in slope to appear on the curve representing the pressure under the canvas as a function of time. The time recorded at this break in slope, expressed in seconds, corresponds to the draining time. The shorter the time, the better the vacuum drainage. The results obtained are shown in FIG. 2 (Vacuum drainage performance at 1 kg/mt and 1.5 kg/mt).

The polymers according to the invention P1 to P4 make it possible to obtain significantly better vacuum drainage performance than that of the CE4 polymer of fossil origin.

B/Performance in DSR Application (Dry Strength), Grammage at 90 g·m$^{-2}$

The paper forms are made with an automatic dynamic form. First, the paper pulp is prepared by disintegrating 90 grams of virgin kraft fibers in 2 liters of hot water for 30 minutes. The pulp obtained is then diluted to a total volume of 9 liters. Once the consistency has been precisely measured, the necessary quantity of this pulp is removed so as to obtain, in the end, a sheet with a weight of 90 g/m2.

The pulp is then introduced into the vat of the dynamic sheet former and is stirred moderately with a mechanical stirrer in order to homogenize the fibrous suspension.

In manual mode, the pulp is pumped up to the level of the nozzle in order to prime the circuit. A blotter and the forming cloth are placed in the bowl of the dynamic sheet former before starting the rotation of the bowl at 1000 m/min and building the water wall. Various dry strength agents are then introduced into the stirred fibrous suspension with a contact time of 30 to 45 seconds for each polymer. The sheet is then produced (in automatic mode) by 22 round trips of the nozzle projecting the pulp into the wall of water. Once the water is drained and the automatic sequence is complete, the forming fabric with the formed fiber network is removed from the bowl of the dynamic former and placed on a table. A dry blotter is laid on the side of the wet fiber mat and is pressed once with a roller. The whole is turned over and the canvas is delicately separated from the fibrous mattress. A second dry blotter is placed and the sheet (between the two blotters) is pressed once under a press delivering 4 bars and is then dried on a tense dryer for 9 min at 117° C. The two blotters are then removed and the sheet is stored overnight in a room with controlled humidity and temperature (50% relative humidity and 23° C.). The wet and dry strength properties of all sheets obtained by this procedure are then evaluated as follows.

The burst (Burst index) is measured with a Messmer Buchel M 405 burst tester according to the TAPPI T403 om-02 standard. The result is expressed in kPa. The bursting index, expressed in kPa·m2/g, is determined by dividing this value by the basis weight of the sheet tested. Results are expressed as percent improvement over blank (Table 7).

Dry tensile strength is measured in the machine direction with a Testometric AX tensile device according to TAPPI T494 om-01. The measurement is expressed in km, and is expressed as a percentage improvement over blank (Table 7).

TABLE 7

| Polymer | Burst Index Polymer dosage | | Dry traction (breaking length) (km) Polymer dosage | |
| --- | --- | --- | --- | --- |
|  | 1 kg/mt | 1.5 kg/mt | 1 kg/mt | 1.5 kg/mt |
| CE4 | 17 | 21 | 24 | 21 |
| P1 | 20 | 24 | 31 | 23 |
| P2 | 22 | 26 | 34 | 23 |
| P3 | 23 | 27 | 37 | 24 |
| P4 | 24 | 27 | 40 | 25 |

(CE = counter-example)

The applicant observes that in addition to better drainage performance, polymers P1 to P4 according to the invention exhibit dry strength performance at least equivalent or even better than that of the comparative polymer CE4.

What is claimed is:

1. A method for obtaining N-vinylformamide comprising reaction between an acetaldehyde and a formamide, wherein the acetaldehyde and/or the formamide comprises $^{14}$C, such that the acetaldehyde and/or the formamide comprises a bio-sourced carbon content of between 40 wt % and 100 wt % relative to total carbon mass of the acetaldehyde and/or the formamide, respectively, wherein the $^{14}$C and the bio-sourced carbon content are measured by a standard ASTM D6866-21Method B.

2. The method according to claim 1, characterized-in wherein the N-vinylformamide has a bio-sourced carbon content of between 40 wt % and 100 wt % relative to the total carbon mass in said N-vinylformamide, the bio-sourced carbon content of the N-vinylformamide is measured according to the standard ASTM D6866-21Method B.

3. The method according to claim 1, wherein the method is a method for obtaining N-vinylformamide by an alkoxy process, methanol being used as a protective agent, said method comprising a thermal decomposition of N-methoxyethylformamide at a temperature between 200° C. and 600° C. and at atmospheric pressure or under a partial vacuum.

* * * * *

UNITED STATES PATENT AND TRADEMARK OFFICE
CERTIFICATE OF CORRECTION

| | |
|---|---|
| PATENT NO. | : 12,269,789 B2 |
| APPLICATION NO. | : 18/566281 |
| DATED | : April 8, 2025 |
| INVENTOR(S) | : Cedrick Favero et al. |

It is certified that error appears in the above-identified patent and that said Letters Patent is hereby corrected as shown below:

In the Specification

Column 4, Line 22, delete "accuracy of 1.10-15." and insert -- accuracy of $1.10^{-15}$. --.

Column 11, Line 15, delete "this section" and insert -- this section. --.

Column 12, Line 13, delete "aryl sulfonates" and insert -- aryl sulfonates. --.

Signed and Sealed this
Nineteenth Day of August, 2025

Coke Morgan Stewart
*Acting Director of the United States Patent and Trademark Office*